United States Patent
Zhang et al.

(10) Patent No.: US 12,360,085 B2
(45) Date of Patent: Jul. 15, 2025

(54) QUANTUM-ENHANCED ALL-OPTICAL PHOTOACOUSTIC SIGNAL DETECTION DEVICE AND METHOD

(71) Applicant: SHANXI UNIVERSITY, Taiyuan (CN)

(72) Inventors: Kuanshou Zhang, Taiyuan (CN); Zheng Song, Taiyuan (CN); Yuanji Li, Taiyuan (CN); Jinxia Feng, Taiyuan (CN)

(73) Assignee: SHANXI UNIVERSITY, Taiyuan (CN)

( * ) Notice: Subject to any disclaimer, the term of this patent is extended or adjusted under 35 U.S.C. 154(b) by 390 days.

(21) Appl. No.: 18/115,356

(22) Filed: Feb. 28, 2023

(65) Prior Publication Data
US 2024/0077457 A1 Mar. 7, 2024

(30) Foreign Application Priority Data
Sep. 6, 2022 (CN) .......................... 202211086309.8

(51) Int. Cl.
*G01N 21/01* (2006.01)
*G01J 3/453* (2006.01)
*G01N 21/62* (2006.01)
*G01N 21/63* (2006.01)
*G01N 29/24* (2006.01)
*G01N 29/30* (2006.01)
*A61B 5/00* (2006.01)

(52) U.S. Cl.
CPC ........ *G01N 29/2418* (2013.01); *G01J 3/4535* (2013.01); *G01N 21/01* (2013.01); *G01N 21/62* (2013.01); *G01N 21/63* (2013.01); *G01N 29/30* (2013.01); *A61B 5/0095* (2013.01)

(58) Field of Classification Search
CPC .... G01N 29/2418; G01N 29/30; G01N 21/01; G01N 21/62; G01N 21/63; G01J 3/4535; A61B 5/0095
See application file for complete search history.

(56) References Cited

FOREIGN PATENT DOCUMENTS

CN 114813699 B * 3/2023

OTHER PUBLICATIONS

English translation on CN-11481369 accessed from worldwide.espacenet.com*

* cited by examiner

*Primary Examiner* — Kristina M Deherrera
*Assistant Examiner* — Jean F Morello

(57) ABSTRACT

The present disclosure belongs to the field of photoacoustic signal detection, and specifically relates to a quantum-enhanced all-optical photoacoustic signal detection device and method. The problem of low sensitivity of photoacoustic signals based on interference measurement is solved, and high-sensitivity detection of photoacoustic signals generated by living organisms including human bodies can be achieved. A degenerate optical parametric oscillator based on a first-type phase matching crystals is used for preparing a vacuum squeezed state light field, a coherent control technology is used for locking the squeezed angle to obtain the quadrature phase vacuum squeezed state, the prepared quadrature phase vacuum squeezed state light field is injected into the vacuum channel of a Michelson interferometer, and a balanced homodyne detection mode is used for achieving detection of the quantum-enhanced photoacoustic signals.

2 Claims, 2 Drawing Sheets

QUANTUM-ENHANCED ALL-OPTICAL PHOTOACOUSTIC SIGNAL DETECTION DEVICE AND METHOD

CROSS-REFERENCE TO RELATED APPLICATION

This patent application claims the benefit and priority of Chinese Patent Application No. 202211086309.8, filed with the China National Intellectual Property Administration on Sep. 6, 2022, the disclosure of which is incorporated by reference herein in its entirety as part of the present application.

TECHNICAL FIELD

The present disclosure belongs to the field of photoacoustic signal detection, and specifically relates to a quantum-enhanced all-optical photoacoustic signal detection device and method.

BACKGROUND

Photoacoustic imaging (PAI) is a hybrid imaging method relying on the photoacoustic effect. According to the working principle of photoacoustic imaging, pulse laser energy is absorbed to generate ultrasonic waves through an exogenous contrast agent or endogenous molecules in biological tissues, and tissue images are obtained by sounding the ultrasonic waves. By utilizing the characteristics of optical excitation and acoustic detection, PAI breaks through the diffusion limit (~1 mm) of high-resolution optical imaging, the structure and function information of the biological tissues can be effectively obtained, a powerful imaging tool is provided for researching the morphological structure, physiological characteristics and metabolic functions of the biological tissues, and the method has a very important position in the field of biomedical imaging.

Ultrasonic sounding plays a crucial role in PAI. Firstly, the bandwidth of a photoacoustic signal excited by short pulse laser is very wide, and only ultrasonic waves with narrow frequency bands need to be detected in ultrasonic imaging. And then, the generation of photoacoustic signals is limited by the maximum permissible exposure (MPE) of the biological tissues, so the photoacoustic signals generated in vivo can be three orders of magnitude weaker than ultrasound signals in ultrasound imaging. Therefore, the detection of photoacoustic signals is the key to achieve high-quality PAI.

Optical ultrasonic detection method is an important detection method. In an all-optical PAI system, ultrasonic generation and detection are completed by optical elements. Compared with a piezoelectric transducer, optical ultrasonic detector is easier to miniaturize, and also can provide a large receiving angle, sensitivity irrelevant to the size of a detector and a wider detective bandwidth. Therefore, the method has good application prospects in the field of biomedicine. Detection sensitivity is a key parameter for evaluating the performance of an optical ultrasonic detector. And noise equivalent pressure (NEP) is usually used for quantification. The NEP can be expressed as pressure in per unit frequency band and represents the noise amplitude in the signal detection process. The small NEP is helpful for obtaining a high signal-to-noise ratio (SNR). Especially, in medical applications, high-sensitivity detection methods are needed to accurately detect signals generated by deep tissues.

At present, all-optical photoacoustic detectors based on optical interferometry measurement can be mainly divided into resonance type optical photoacoustic detectors and non-resonance type optical photoacoustic detectors. The resonance type optical photoacoustic detector comprises an optical fiber Fabry-Perot cavity, a micro-ring, a Bragg grating waveguide and the like, and optical resonant cavities with very high quality factors are needed to be constructed on optical fibers or waveguides. The processing technology is complex, the manufacturing difficulty is high, and the production cost is expensive. The non-resonance type optical photoacoustic detector mainly comprises a Michelson interferometer, a Mach-Zehnder interferometer and a Doppler interferometer. The basic principles of the non-resonance type optical photoacoustic detector are realized by measuring laser phase change caused by photoacoustic waves generated by an absorber. The device is very simple in structure, but NEP can only reach the magnitude of Pa/√Hz, and weak signals generated by deep tissues cannot be accurately measured, so that the application of the device in biomedical imaging requiring high-sensitivity detection is limited.

A method for measuring photoacoustic signals based on an optical interference principle is widely applied to PAI, but for signals with weak intensity, the method still cannot perform accurate detection. Although the detection signal-to-noise ratio can be improved by increasing the laser power of probe light, the increase of the laser power results in extra noise generated in the photo-thermal conversion process and is not beneficial to detection of photoacoustic signals. The Michelson interferometer can detect photoacoustic signals by interaction between an acoustic field and an optical path. Although the detection sensitivity can be improved to a certain degree by increasing the propagation length of laser in water to enhance the interaction, the stability of the system becomes worse. Therefore, an existing all-optical photoacoustic imaging device based on Michelson interferometer interferometry cannot be applied to imaging of samples with deep absorbers and living animals in practice.

Therefore, there is an urgent need in the art for a device and a method for detecting all-optical photoacoustic signals, and the device and the method are high in sensitivity without affecting other imaging indexes.

SUMMARY

Aiming at the problems, the present disclosure provides a quantum-enhanced all-optical photoacoustic signal detection device and method, the problem that photoacoustic signals during optical interference type measurement is low in sensitivity is solved, and high-sensitivity detection of weak photoacoustic signals generated by living organisms including human bodies can be achieved. The core of the present disclosure is that after the classical technology is utilized for enhancing the detection sensitivity to the maximum extent, a quantum light field is applied to break through the limit of shot noise. On the premise that other imaging indexes are not affected, all-optical photoacoustic signal detection with higher sensitivity can be achieved.

In order to achieve the above purpose, the present disclosure adopts the following technical scheme.

A quantum-enhanced all-optical photoacoustic signal detection device comprises a continuous wave single-frequency dual-wavelength laser, a first dichroscope, a first plane mirror, a second dichroscope, an input coupling mirror, a nonlinear crystal, a second plane mirror, a third plane mirror, an optical beam splitter, a plane mirror adhered with piezoelectric ceramic, a water tank, a fourth plane mirror, a fifth plane mirror, an optical isolator and a balanced homodyne detector;

the continuous wave single-frequency dual-wavelength laser outputs two laser beams with different wavelengths, one laser beam is used as probe light to penetrate through the first dichroscope, the other laser beam is used as pump light to be reflected by the first dichroscope, the probe light is injected into a Michelson interferometer composed of the optical beam splitter, the plane mirror adhered with piezoelectric ceramic and the fourth plane mirror, the probe light is divided into two parts by the optical beam splitter, one part of light reflected by the optical beam splitter serves as reference light and is reflected back to an original light path through the plane mirror adhered with piezoelectric ceramic, the other part of light transmitted by the optical beam splitter serves as signal light, penetrates through the water tank and is reflected back to the original light path through the fourth plane mirror, the two laser beams are interfered on the optical beam splitter, and the interfered laser is reflected by the fifth plane mirror and input into the optical isolator;

the pump light is reflected by the first plane mirror, penetrates through the second dichroscope and then enters an optical parametric oscillator composed of the input coupling mirror and the nonlinear crystal, and a quadrature phase vacuum squeezed state light field output by the optical parametric oscillator is reflected by the second dichroscope, the second plane mirror and the third plane mirror in sequence and then enters the optical isolator, the vacuum channel of the Michelson interferometer is filled with the quadrature phase vacuum squeezed state light field through the optical isolator, and the balanced homodyne detector is used for detecting photoacoustic signals to achieve detection of the quantum-enhanced all-optical photoacoustic signals;

the water tank is filled with water, and an object to be measured is located in the water tank.

A quantum-enhanced all-optical photoacoustic signal detection method based on the device comprises the following steps:

S1, taking one laser beam output by a continuous wave single-frequency dual-wavelength laser as pump light, enabling the pump light to enter an optical parametric oscillator composed of an input coupling mirror and a nonlinear crystal through a second dichroscope after being reflected by a first dichroscope and a first plane mirror, and operating the optical parametric oscillator under a threshold value to obtain a vacuum squeezed state light field;

S2, locking a squeezed angle of the vacuum squeezed state light field, locking a relative phase between the pump light and the vacuum squeezed state light field, enabling the optical parametric oscillator to output a quadrature phase vacuum squeezed state light field, and enabling the quadrature phase vacuum squeezed state light field to enter an optical isolator after being reflected by the second dichroscope, a second plane mirror and a third plane mirror in sequence;

S3, taking the other laser beam output by the continuous wave single-frequency dual-wavelength laser as probe light, injecting the probe light into a Michelson interferometer composed of an optical beam splitter, a plane mirror adhered with piezoelectric ceramic and a fourth plane mirror after penetrating through the first dichroscope, dividing the probe light into two parts by the optical beam splitter, taking the light reflected by the optical beam splitter as reference light, reflecting the reference light back to the original light path through the plane mirror adhered with piezoelectric ceramic, taking the light transmitted by the optical beam splitter as signal light, reflecting the signal light back to the original light path through the fourth plane mirror after penetrating through the water tank, interfering the two laser beams on the optical beam splitter, and inputting the interfered laser into the optical isolator after penetrating through the fifth plane mirror;

S4, filling a vacuum channel of the Michelson interferometer with the quadrature phase vacuum squeezed state light field by the reflection end of the optical isolator to achieve the quantum-enhanced Michelson interferometer;

S5, irradiating an object to be measured with exciting light so that an absorber in the object to be measured absorbs energy to thermally expand to generate ultrasonic waves, propagating the ultrasonic waves in water and changing the refractive index of water so that the change of the refractive index of water causes the change of the phases of two arms of the Michelson interferometer, and finally changing the light intensity of laser at the output end of the Michel son interferometer;

S6, enabling the laser at the output end of the Michelson interferometer to penetrate through the optical isolator, and then using a balanced homodyne detector to detect photoacoustic signals so as to achieve detection of quantum-enhanced all-optical photoacoustic signals.

Compared with the prior art, the present disclosure has the following advantages.

Firstly, the transmission light paths of the probe light and the exciting light are separated, the exciting light is incident into an object to be imaged, the probe light does not need to irradiate the object to be measured, and the exciting light can irradiate the object to be measured with the maximum laser power within the MPE (Maximum Permissible Exposure) range so as to excite the strongest photoacoustic signal.

Secondly, signal light penetrates through the water tank twice, so that the interaction between the signal light and a sound field is enhanced, and the detection sensitivity is improved.

Thirdly, on the basis of obtaining the maximum photoacoustic signal detection signal-to-noise ratio by utilizing the classical technology, the quadrature phase vacuum squeezed state light field is injected into the vacuum channel of the Michelson interferometer, and the sensitivity of photoacoustic signal measurement is further improved. Moreover, quantum-enhanced photoacoustic signals are obtained by using a balanced homodyne detection mode.

Fourthly, the detection device is suitable for detection of any photoacoustic signal.

Fifthly, compared with a traditional optical interference method for measuring the photoacoustic signals, the method provided by the present disclosure can obviously improve the detection sensitivity of the photoacoustic signals under the condition of the same laser power.

Sixthly, compared with a method for enhancing the detection sensitivity by increasing the area of a detection element in a photoacoustic transducer, the method can ensure the detection sensitivity and the spatial resolution at the same time and is more suitable for high-sensitivity imaging of a living biological sample.

Reference signs: 1, continuous wave single-frequency dual-wavelength laser; 2, first dichroscope; 3, first plane mirror; 4, second dichroscope; 5, input coupling mirror; 6, nonlinear crystal; 7, second plane mirror; 8, third plane mirror; 9, optical beam splitter; 10, plane mirror adhered with piezoelectric ceramic; 11, object to be measured; 12, water tank; 13, fourth plane mirror; 14, fifth plane mirror; 15, optical isolator; and 16, balanced homodyne detector.

Figure 1:
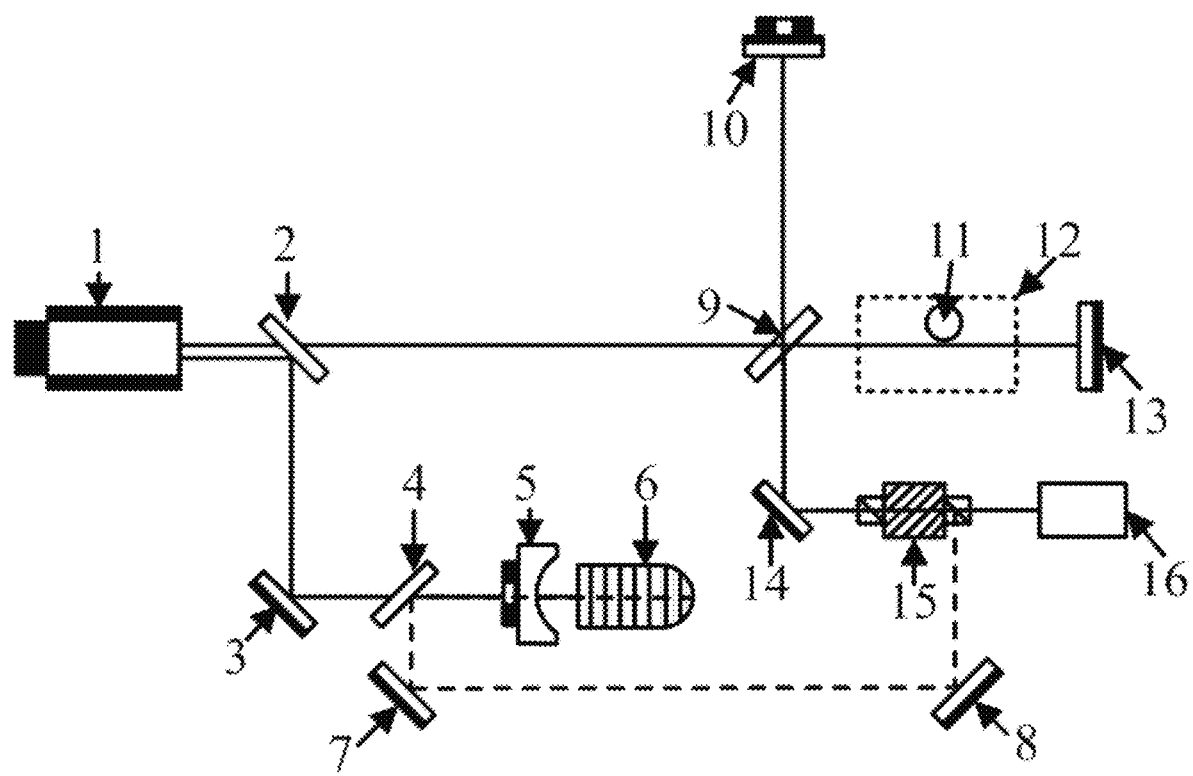
FIG. 1 is a schematic diagram of a quantum-enhanced all-optical photoacoustic signal detection device in the present disclosure.
Figure 2:
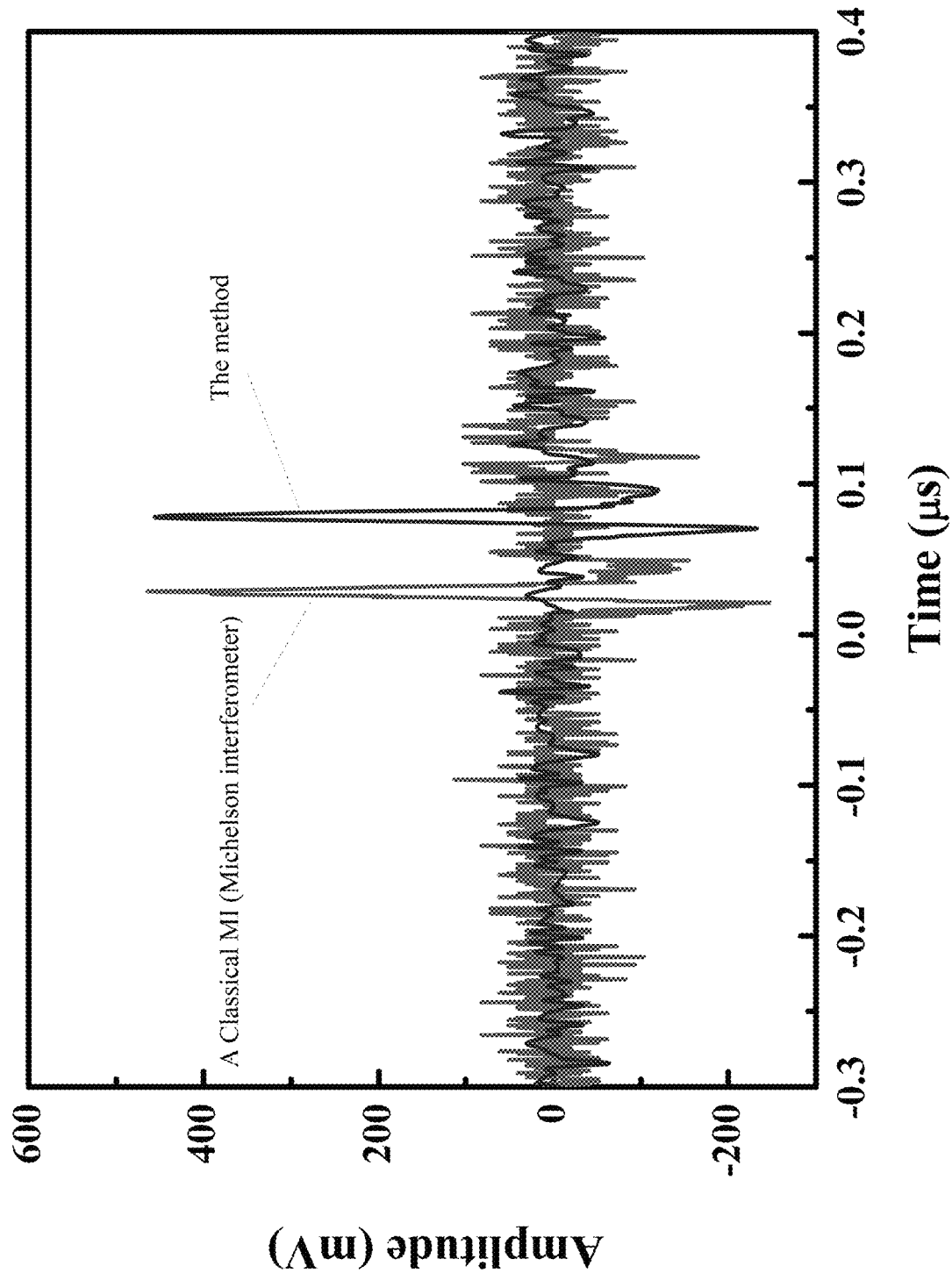

FIG. 2 is a graph of improvement on SNR (Signal Noise Ratio) of photoacoustic signals in the present disclosure.

DETAILED DESCRIPTION OF THE EMBODIMENTS

Embodiment I

A quantum-enhanced all-optical photoacoustic signal detection device comprises a continuous wave single-frequency dual-wavelength laser 1, a first dichroscope 2, a first plane mirror 3, a second dichroscope 4, an input coupling mirror 5, a nonlinear crystal 6, a second plane mirror 7, a third plane mirror 8, an optical beam splitter 9, a plane mirror 10 adhered with piezoelectric ceramic, a water tank 12, a fourth plane mirror 13, a fifth plane mirror 14, an optical isolator 15 and a balanced homodyne detector 16.

In the embodiment, the continuous wave single-frequency dual-wavelength laser 1 is a 1064 nm/532 nm continuous wave single-frequency dual-wavelength laser. The first dichroscope 2 is a HT (High Transmission) @1064 nm & HR (High Reflection) @532 nm plane mirror. The first plane mirror 3 is a 45° HR@532 nm plane mirror. The second dichroscope 4 is a HR@1064 nm & HT@532 nm plane mirror. The second plane mirror 7 is a 45° HR@1064 nm plane mirror. The third plane mirror 8 is a 45° HR@1064 nm plane mirror. The plane mirror 10 adhered with piezoelectric ceramic is a 0° HR@1064 nm plane mirror. The fourth plane mirror 13 is a 0° HR@1064 nm plane mirror. The fifth plane mirror 14 is a 45° HR@1064 nm plane mirror.

The input coupling mirror 5 is a plano-concave lens. The radius of curvature of the concave surface is 25 mm. The film coating parameters T of the concave surface are equal to 13%@1.06 μm and 80%@532 nm. The film coating parameter R of the plane is smaller than 0.2%@1.06 μm & 532 nm. The nonlinear crystal 6 is a periodically poled $KTiOPO_4$ (PPKTP) crystal.

The continuous wave single-frequency dual-wavelength laser 1 outputs two laser beams with different wavelengths (1064 nm and 532 nm). One laser beam with the wavelength of 1064 nm is used as probe light to penetrate through the first dichroscope 2. The other laser beam with the wavelength of 532 nm is used as pump light to be reflected by the first dichroscope 2. The probe light is injected into a Michelson interferometer composed of the optical beam splitter 9, the plane mirror 10 adhered with piezoelectric ceramic and the fourth plane mirror 13. The probe light is divided into two parts by the optical beam splitter 9. One part of light reflected by the optical beam splitter 9 serves as reference light and is reflected back to an original light path by the plane mirror 10 adhered with piezoelectric ceramic. The other part of light transmitted by the optical beam splitter 9 serves as signal light, penetrates through the water tank 12 and is reflected back to the original light path by the fourth plane mirror 13. The two laser beams are interfered on the optical beam splitter 9, and the interfered laser is reflected by the fifth plane mirror 14 and input into the optical isolator 15.

The pump light is reflected by the first plane mirror 3, penetrates through the second dichroscope 4 and then enters an optical parametric oscillator composed of the input coupling mirror 5 and the nonlinear crystal 6. A quadrature phase vacuum squeezed state light field output by the optical parametric oscillator is reflected by the second dichroscope 4, the second plane mirror 7 and the third plane mirror 8 in sequence and then enters the optical isolator 15. The vacuum channel of the Michelson interferometer is filled with the quadrature phase vacuum squeezed state light field by the optical isolator 15. The balanced homodyne detector 6 is used for detecting photoacoustic signals to achieve detection of the quantum-enhanced all-optical photoacoustic signals.

The water tank 12 is filled with water, and an object 11 to be measured is located in the water tank 12.

A quantum-enhanced all-optical photoacoustic signal detection method based on the device comprises the following steps:

S1, taking one laser beam output by a continuous wave single-frequency dual-wavelength laser 1 as pump light, enabling the pump light to enter a degenerate optical parametric oscillator (DOPO) composed of an input coupling mirror 5 and a nonlinear crystal 6 through a second dichroscope 4 after being reflected by a first dichroscope 2 and a first plane mirror 3, and operating the optical parametric oscillator under a threshold value to obtain a vacuum squeezed state light field with the wavelength of 1064 nm (the threshold value of the optical parametric oscillator is about 55 mW, and when the power of the pump light is smaller than the threshold value, the cavity of the DOPO outputs the vacuum squeezed state light field with the wavelength of 1064 nm);

S2, locking the squeezed angle of the vacuum squeezed state light field, locking the relative phase between the pump light and the vacuum squeezed state light field, enabling the optical parametric oscillator to output a quadrature phase vacuum squeezed state light field, and enabling the quadrature phase vacuum squeezed state light field to enter an optical isolator 15 after being reflected by the second dichroscope 4, a second plane mirror 7 and a third plane mirror 8 in sequence;

S3, taking the other laser beam output by the continuous wave single-frequency dual-wavelength laser 1 as probe light, injecting the probe light into a Michelson interferometer composed of an optical beam splitter 9, a plane mirror 10 adhered with piezoelectric ceramic and a fourth plane mirror 13 after penetrating through the first dichroscope 2, dividing the probe light into two parts by the optical beam splitter 9, taking the light reflected by the optical beam splitter 9 as reference light, reflecting the reference light back to the original light path through the plane mirror 10 adhered with piezoelectric ceramic, taking the light transmitted by the optical beam splitter 9 as signal light, reflecting the signal light back to the original light path through the fourth plane mirror 13 after penetrating through the water tank 12, interfering the two laser beams on the optical beam splitter 9, and inputting the interfered laser into the optical isolator 15 after being reflected by the fifth plane mirror 14;

S4, filling the vacuum channel of the Michelson interferometer with the quadrature phase vacuum squeezed state light field with the wavelength of 1064 nm by the optical isolator 15 to achieve the quantum-enhanced Michelson interferometer (MI);

S5, irradiating an object 11 to be measured with exciting light which is pulsed light with the central wavelength of 532 nm, the pulse width of 1 ns and the pulse energy of 1 μJ so that an absorber in the object 11 to be measured absorbs energy to thermally expand to generate ultrasonic waves, propagating the ultrasonic waves in water and changing the refractive index of water so that the change of the refractive index of water causes the change of the phases of two arms of the Michelson interferometer (MI), and finally changing the light intensity of laser at the output end of the Michelson interferometer (MI);

S6, enabling the laser at the output end of the Michelson interferometer (MI) to penetrate through the optical isolator 15, and then using a balanced homodyne detector 16 to detect photoacoustic signals so as to achieve detection of quantum-enhanced all-optical photoacoustic signals. The measurement of the photoacoustic signals capable of breaking through the limit of shot noise is completed by utilizing the quantum-enhanced Michelson interferometer (MI). As shown in FIG. 2, compared with a classical MI, the SNR of the photoacoustic signals measured by the method is improved by 2 dB.

What is claimed is:

1. A quantum-enhanced all-optical photoacoustic signal detection device, comprising a continuous wave single-frequency dual-wavelength laser, a first dichroscope, a first plane mirror, a second dichroscope, an input coupling mirror, a nonlinear crystal, a second plane mirror, a third plane mirror, an optical beam splitter, a plane mirror adhered with piezoelectric ceramic, a water tank, a fourth plane mirror, a fifth plane mirror, an optical isolator and a balanced homodyne detector;

the continuous wave single-frequency dual-wavelength laser outputs two laser beams with different wavelengths, one laser beam is used as probe light to penetrate through the first dichroscope, the other laser beam is used as pump light to be reflected by the first dichroscope, the probe light is injected into a Michelson interferometer composed of the optical beam splitter, the plane mirror adhered with piezoelectric ceramic and the fourth plane mirror, the probe light is divided into two parts by the optical beam splitter, one part of light reflected by the optical beam splitter serves as reference light and is reflected back to an original light path through the plane mirror adhered with piezoelectric ceramic, the other part of light transmitted by the optical beam splitter serves as signal light, penetrates through the water tank and is reflected back to the original light path by the fourth plane mirror, the two laser beams are interfered on the optical beam splitter, and the interfered laser is reflected by the fifth plane mirror and input into the optical isolator;

the pump light is reflected by the first plane mirror, penetrates through the second dichroscope and then enters an optical parametric oscillator composed of the input coupling mirror and the nonlinear crystal, and a quadrature phase vacuum squeezed state light field output by the optical parametric oscillator is reflected by the second dichroscope, the second plane mirror and the third plane mirror in sequence and then enters the optical isolator, a vacuum channel of the Michelson interferometer is filled with the quadrature phase vacuum squeezed state light field through the optical isolator, and the balanced homodyne detector is used for detecting photoacoustic signals to achieve detection of the quantum-enhanced all-optical photoacoustic signals;

the water tank is filled with water, and an object to be measured is located in the water tank.

2. A quantum-enhanced all-optical photoacoustic signal detection method based on the device according to claim 1, comprising the following steps:

S1, taking one laser beam output by a continuous wave single-frequency dual-wavelength laser as pump light, enabling the pump light to enter an optical parametric oscillator composed of an input coupling mirror and a nonlinear crystal through a second dichroscope after being reflected by a first dichroscope and a first plane mirror, and operating the optical parametric oscillator under a threshold value to obtain a vacuum squeezed state light field;

S2, locking a squeezed angle of the vacuum squeezed state light field, locking a relative phase between the pump light and the vacuum squeezed state light field, enabling the optical parametric oscillator to output a quadrature phase vacuum squeezed state light field, and enabling the quadrature phase vacuum squeezed state light field to enter an optical isolator after being reflected by the second dichroscope, the second plane mirror and the third plane mirror in sequence;

S3, taking the other laser beam output by the continuous wave single-frequency dual-wavelength laser as probe light, injecting the probe light into a Michelson interferometer composed of an optical beam splitter, a plane mirror adhered with piezoelectric ceramic and the fourth plane mirror after penetrating through the first dichroscope, dividing the probe light into two parts by the optical beam splitter, taking the light reflected by the optical beam splitter as reference light, reflecting the reference light back to an original light path through the plane mirror adhered with piezoelectric ceramic, taking the light transmitted by the optical beam splitter as signal light, reflecting the signal light back to the original light path through the fourth plane mirror after penetrating through the water tank, interfering the two laser beams on the optical beam splitter, and inputting the interfered laser into the optical isolator after being reflected by the fifth plane mirror;

S4, filling the vacuum channel of the Michelson interferometer with the quadrature phase vacuum squeezed state light field by the reflection end of the optical isolator to achieve the quantum-enhanced Michelson interferometer;

S5, irradiating an object to be measured with exciting light so that an absorber in the object to be measured absorbs energy to thermally expand to generate ultrasonic waves, propagating the ultrasonic waves in water and changing the refractive index of water so that the change of the refractive index of water causes the change of the phases of two arms of the Michelson interferometer, and finally changing the light intensity of laser at the output end of the Michelson interferometer;

S6, enabling the laser at the output end of the Michelson interferometer to penetrate through the optical isolator, and then using a balanced homodyne detector to detect photoacoustic signals so as to achieve detection of quantum-enhanced all-optical photoacoustic signals.

* * * * *